(12) United States Patent
Guo et al.

(10) Patent No.: US 8,507,010 B2
(45) Date of Patent: *Aug. 13, 2013

(54) COMPOSITIONS COMPRISING QUINAZOLINE DERIVATIVES

(75) Inventors: Jianhui Guo, Shanghai (CN); Haiying He, Shanghai (CN)

(73) Assignee: Shanghai Allist Pharmaceuticals, Inc. (CN)

( * ) Notice: Subject to any disclaimer, the term of this patent is extended or adjusted under 35 U.S.C. 154(b) by 62 days.

This patent is subject to a terminal disclaimer.

(21) Appl. No.: 12/993,629

(22) PCT Filed: May 21, 2009

(86) PCT No.: PCT/CN2009/000557
§ 371 (c)(1),
(2), (4) Date: Jan. 6, 2011

(87) PCT Pub. No.: WO2009/140863
PCT Pub. Date: Nov. 26, 2009

(65) Prior Publication Data
US 2011/0111059 A1    May 12, 2011

(30) Foreign Application Priority Data
May 21, 2008  (CN) .......................... 2008 1 0043382

(51) Int. Cl.
| A61K 31/517 | (2006.01) |
| A61K 33/24 | (2006.01) |
| A61P 35/00 | (2006.01) |
| A61P 27/02 | (2006.01) |
| A61P 9/10 | (2006.01) |
| A61P 29/00 | (2006.01) |
| A61P 17/06 | (2006.01) |
| A61P 11/00 | (2006.01) |

(52) U.S. Cl.
USPC ........................................ 424/649; 514/266.4

(58) Field of Classification Search
None
See application file for complete search history.

(56) References Cited

U.S. PATENT DOCUMENTS

| 4,639,454 | A | * | 1/1987 | Hesson | ....................... 514/266.1 |
| 5,457,105 | A |  | 10/1995 | Barker |  |
| 5,521,184 | A |  | 5/1996 | Zimmermann |  |
| 5,616,582 | A |  | 4/1997 | Barker |  |
| 5,747,498 | A |  | 5/1998 | Schnur et al. |  |
| 5,770,599 | A |  | 6/1998 | Gibson |  |
| 6,391,874 | B1 |  | 5/2002 | Cockerill et al. |  |
| 6,713,485 | B2 |  | 3/2004 | Carter et al. |  |
| 6,727,256 | B1 |  | 4/2004 | Carter et al. |  |
| 6,828,320 | B2 |  | 12/2004 | Cockerill et al. |  |
| 6,894,051 | B1 |  | 5/2005 | Zimmermann et al. |  |
| 6,900,221 | B1 |  | 5/2005 | Norris et al. |  |
| 6,958,335 | B2 |  | 10/2005 | Buchdunger et al. |  |
| 7,157,466 | B2 |  | 1/2007 | McClure et al. |  |
| 8,044,063 | B2 | * | 10/2011 | Guo et al. | ................... 514/266.4 |
| 2002/0010188 | A1 | * | 1/2002 | Basford et al. | ................ 514/260 |
| 2003/0139398 | A1 | * | 7/2003 | Hoekstra et al. | ........... 514/224.2 |
| 2004/0002505 | A1 | * | 1/2004 | Ozawa et al. | ............. 514/259.1 |
| 2007/0104721 | A1 | * | 5/2007 | Moore et al. | ............... 424/155.1 |
| 2008/0300248 | A1 | * | 12/2008 | Guo et al. | ................... 514/234.5 |
| 2009/0069316 | A1 | * | 3/2009 | Hong et al. | ................ 514/233.5 |

FOREIGN PATENT DOCUMENTS

| CN | 1077713 A | 10/1993 |
| CN | 1182421 A | 5/1998 |
| CN | 1264375 A | 8/2000 |
| CN | 1292788 A | 4/2001 |
| CN | 1440403 A | 9/2003 |
| CN | 1622808 A | 6/2005 |
| CN | 1636992 A | 7/2005 |
| CN | 1656081 A | 8/2005 |
| CN | 101003514 A | 7/2007 |
| CN | 101544609 A | 9/2009 |
| EP | 0564409 A1 | 3/1993 |
| EP | 1990337 A1 | 11/2008 |
| EP | 226994 A1 | 1/2011 |
| WO | WO 96/30347 A1 | 10/1996 |
| WO | WO 96/33980 A1 | 10/1996 |
| WO | WO97/38983 | 10/1997 |
| WO | WO 97/38983 A1 | 10/1997 |
| WO | WO 99/03854 A1 | 1/1999 |
| WO | WO 99/35146 A1 | 7/1999 |
| WO | WO 00/06555 A1 | 2/2000 |
| WO | WO 02/02552 A1 | 1/2002 |
| WO | WO 02/34727 A2 | 5/2002 |
| WO | WO 03/082831 A1 | 10/2003 |
| WO | WO2006/071017 | 7/2006 |

(Continued)

OTHER PUBLICATIONS

U.S. Pharmacopeia, pp. 1-16 of chapter 1231 (2008).*
International Search Report for corresponding PCT application No. PCT/CN2009/000557, mail date Aug. 27, 2009.
Supplementary European Search Report for corresponding EP Application No. EP09749406, Aug. 28, 2012.
Fussnegger, Lutrol® F 68 BASF product info, BASF ExAct, Nov. 3, 1999, pp. 5-6.
Liu Hui, Effect of Amylum Pregelatinisatum on the Dissolution of Calcium Dobesilate Capsule, China Pharmacy, Jan. 1, 2008, 2 pages, Abstract Only.

(Continued)

*Primary Examiner* — Patricia A Duffy
*Assistant Examiner* — Garen Gotfredson
(74) *Attorney, Agent, or Firm* — Myers Bigel Sibley & Sajovec, P.A.

(57) ABSTRACT

The present invention provides a pharmaceutical composition, useful for the treatment of diseases characterized by abnormal PTKs activity of erbB family in a mammal, comprising pharmaceutically acceptable salts of N-{4-[3-chloro-4-(3-fluoro-benzyloxy) phenylamino]quinazolin-6-yl}-acrylamide, optionally a pharmaceutically applicable carrier or diluent, and a stabilizer having a dispersing and/or protective effect on the active ingredient. The present invention further provides a pharmaceutical formulation comprising said composition, methods for preparation of said composition and said formulation, as well as use of said composition and said formulation for treating diseases characterized by abnormal PTKs activity of erbB family in a mammal.

27 Claims, No Drawings

(56) References Cited

FOREIGN PATENT DOCUMENTS

| WO | WO2006/071017 A1 | 7/2006 |
| WO | WO2007/082434 | 7/2007 |
| WO | WO2007/082434 A1 | 7/2007 |
| WO | WO2008/098485 | 8/2008 |
| WO | WO2008/098485 A1 | 8/2008 |
| WO | WO2009/012702 | 1/2009 |
| WO | WO 2009/117899 | 10/2009 |

* cited by examiner

COMPOSITIONS COMPRISING QUINAZOLINE DERIVATIVES

CROSS REFERENCE TO RELATED APPLICATIONS

This application is a 35 U.S.C. §371 national phase application of PCT Application No. PCT/CN2009/000557, filed on May 21, 2009, which claims priority from Chinese Patent Application 200810043382.0, filed on May 21, 2008, the disclosures and contents of which are incorporated by reference herein in their entirety. The above-referenced PCT International Application was published in Chinese as International Publication No. WO2009/140863.

FIELD OF THE INVENTION

The present invention relates to pharmaceutical compositions and formulations comprising salts of the quinazoline derivative N-{4-[3-chloro-4-(3-fluoro-benzyloxy)phenylamino]quinazolin-6-yl}-acrylamide having inhibitory effect against abnormal activity of protein tyrosine kinases (PTKs) of mammalian erbB family, and to preparation method thereof. The present invention also provides use of said compositions in the manufacture of a medicament for treating diseases characterized by abnormal PTKs activity of erbB family in a mammal and use of the said compositions for treating said diseases.

BACKGROUND OF THE INVENTION

PTKs catalyzes phosphorylation of specific tyrosine residues in various proteins, which residues participate in regulation of cellular growth and differentiation (A. F. Wilks, Progress in Growth Factor Research, 1990, 1, 97-111; S. A. Courtneidge, Dev. Supp. L, 1993, 57-64; J. A. Cooper, Semin. Cell Biol.; 1994, 5(6), 377-387; R. F. Paulson, Semin. Immunol., 1995, 7(4), 267-277; A. C. Chan, Curr, Opin. Immunol., 1996, 8(3), 394-401). Much inappropriate or uncontrolled activation of PTKs i.e., abnormal PTK activity, such as overexpression or mutation, leads to uncontrolled cellular growth and thereby causes many diseases. Known diseases include psoriasis, rheumatoid arthritis, bronchitis, and cancers as well as other diseases such as angiogenesis, atherosclerosis, age-related macular degeneration, diabetic retinopathy and the like. At present, erbB family comprising c-erbB-2, EGFr and erbB-4, is a group of PTKs useful as therapeutic targets, and it shows a potential effect in the treatment of over-proliferative diseases in particular, especially in the treatment of human malignant pathological changes e.g., non-small cell lung cancer, bladder cancer, and head and neck cancer. In addition, enhanced c-erbB-2 activity involves breast cancer, ovarian cancer, gastric cancer and pancreatic cancer. Hence, inhibition of PTKs of erbB family provides a therapy for diseases characterized by abnormal PTKs activity of erbB family. Biological action of PTKs of erbB family as well as relationship thereof with various disorders have been discussed in, e.g., the U.S. Pat. No. 5,773,476, WO 99/35146, M. G. Hung et al., Seminars in Oncology, 26:4, Suppl. 12 (August) 1999, 51-59; Ullrich et al., Cell, 61:203-212, Apr., 20, 1990; Modjitahedi et al., Int. J. of Oncology, 13:335-342, 1998; and J. R. Wooburn, Pharmacol. Ther., 82:2-3, 241-250, 1999.

Some documents record the relevant technology in terms of PTKs inhibitors and/or quinazoline derivatives. For example, WO 9630347 (Chinese patent application CN 96102992.7) concerns some 4-(substituted phenylamino) quinazoline derivatives for treating over-proliferative disorders. WO 9738983 (Chinese patent application CN 97194458.X) provides compounds as irreversible inhibitors of tyrosine kinases. WO 0006555 (Chinese patent application CN 99808949.4) discloses that some substituted quinazoline derivatives have PTKs inhibitory activity. WO 9935146 (Chinese patent application CN 99803887.3) discloses bicyclic heteroaromatic compounds as PTKs inhibitors. WO 2006071017 discloses a series of quinazoline compounds. Chinese patent applications CN 01817895.2, CN 93103566.X, CN 98807303.X, CN 96193526.X, CN 01812051.2, CN 99803887.3, CN 200410089867.5, and CN 03811739.8, and US patents such as U.S. Pat. Nos. 5,521,184, 6,894,051, 6,958,335, 5,457,105, 5,616,582, 5,770,599, 5,747,498, 6,900,221, 6,391,874, 6,713,485, 6,727,256, 6,828,320, and 7,157,466 all mention that a plurality of types of quinazoline compounds have PTKs inhibitory activity. Commercially available drugs include FDA approved Laptinib, Gefitinib, Erlotinib, Imatinib etc. These drugs are directed to different indications and the treatment of only a few particular tumors. With the continuous development of medical diagnosis and therapy levels, the therapy of proliferative diseases, in particular tumors, is more and more specific and targeted, so there is an urgent clinical demand for products which are clearly effective and highly targeted on proliferative diseases and tumors.

Novel compounds having an inhibitory effect on mammalian PTKs, having good biological properties and good formulation adaptability and being useful for the preparation of pharmaceutical compositions that meet requirements during formulation process and have storage stability as well as high bioavailability, will undoubtedly promote therapeutic progress of diseases characterized by abnormal PTKs activity of erbB family and satisfy urgent clinical needs.

In the Chinese patent application CN 200610023526.7, submitted by the applicant on Jan. 20, 2006 and published on Jul. 25, 2007, and in the PCT application WO 2007/082434 submitted on Oct. 20, 2006 and published on Jul. 26, 2007, the applicant presents a series of quinazoline compounds having the formula I:

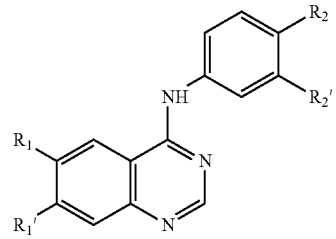

Formula I

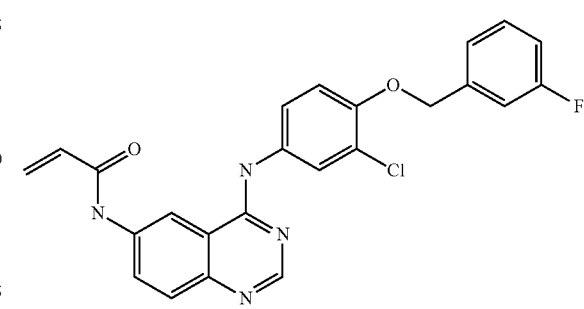

Formula II

Intensive studies and explorations of the applicant reveal that the series of compounds have PTKs inhibitory activity. It is particularly stated that N-{4-[3-chloro-4-(3-fluoro-benzyloxy)phenylamino]quinazolin-6-yl}-acrylamide, as shown in Formula II, has excellent inhibitory activity against erbB-2 kinase. Experiments demonstrate that it has remarkable inhibitory effect on growth of human epidermoid squamous carcinoma cell A431 and human breast cancer cell BT-474 and that it has an obvious anti-tumor effect on human epidermoid squamous carcinoma cell A431 grafted to a nude mouse. These two applications are fully incorporated herein by reference.

After intensive and extensive research and a large amount of tests, the applicant has discovered that salts of N-{-4-[3-chloro-4-(3-fluoro-benzyloxy)phenylamino]quinazolin-6-yl}-acrylamide have very beneficial properties that solve the solubility problem of the compound in oral administration. In PCT/CN2008/000318 submitted on Feb. 4, 2008, the applicant presents the salt form of N-{4-[3-chloro-4-(3-fluoro-benzyloxy)phenylamino]quinazolin-6-yl}-acrylamide. The application is fully incorporated herein by reference.

By further research, the applicant surprisingly found the stabilizers that have dispersing and/or protective effect on the active ingredient, salts of N-{4-[3-chloro-4-(3-fluoro-benzyloxy)phenylamino]quinazolin-6-yl}-acrylamide. These stabilizers are some high-molecular substances and/or surface active substances that can enhance applicability of the active ingredient to a formulation so that a pharmaceutical composition comprising the active ingredient has good formulation adaptability and improves stability of the formulation. Thus, a pharmaceutical formulation which is stable during storage and has high bioavailability has been prepared, and thereby the present invention is accomplished.

CONTENT OF THE INVENTION

The present invention provides a pharmaceutical composition comprising a pharmaceutically acceptable salt of N-{4-[3-chloro-4-(3-fluoro-benzyloxy)phenylamino]quinazolin-6-yl}-acrylamide as an active ingredient and optionally (not compulsorily) a pharmaceutically applicable carrier or diluent (also referred to as auxiliary materials herein), and further comprising a stabilizer having dispersing and/or protective effect on the active ingredient, wherein the ratio by weight of the stabilizer to the active ingredient is 1:0.1 to 10. The present invention further provides a pharmaceutical formulation comprising said composition and a pharmaceutically applicable carrier or diluent. Said composition or formulation has an inhibitory, regulatory and/or controlling effect on signaling of protein tyrosine kinases of mammalian erbB family and shows an excellent therapeutic effect and safety in treating diseases characterized by abnormal PTKs activity of erbB family.

The applicant has discovered that high-molecular substances and/or surface active substances as a stabilizer can improve stability of the formulation. This stabilizer allows uniform dispersion of the active ingredient in a carrier or diluent and meanwhile, the dispersed state can be stably maintained during storage, which is undoubtedly favorable for stability of the pharmaceutical composition/formulation. Presence of the stabilizer avoids change of biological efficacy of the active ingredient caused by change of dispersion degree. Furthermore, in the preparation of a solid formulation involving a compressing process, the stabilizer not only ensures uniform dispersion of the active ingredient in unit formulation so that the prepared formulation has good content homogeneity, but protects the active ingredient during compressing to maintain its original crystalline form, thereby avoiding change of the biological efficacy of the active ingredient caused by the change of parameters. Further, use of the stabilizer surprisingly increases dissolution of the active ingredient and enhances bioavailability of the formulation. Addition of the stabilizer in the preparation of a liquid formulation can not only allow the active ingredient to be fully wet by a solvent and thus well dissolved and dispersed in the solvent, thereby avoiding precipitation of the active ingredient, but enhance compatibility of the active ingredient with further pharmaceutically acceptable carrier materials so that the liquid formulation is in a uniform and stable state. Such state can last for a rather long period of time and benefits storage and use of the composition product.

By tests screening, we have found that the weight ratio of the stabilizer to the pharmacologically active ingredient is 1:0.1 to 10 and that first mixing the stabilizer with the active ingredient in the preparation can lead to a superior stability. Preferred weight ratio of the stabilizer to the pharmacological active ingredient is 1:0.1 to 5, particularly preferred 1:0.2 to 2.

The present invention also provides preparation methods of said pharmaceutical composition and formulation.

The present invention also provides use of said pharmaceutical compositions in the manufacture of a medicament for treating diseases characterized by abnormal PTKs activity of erbB family in a mammal.

The present invention also provides a method for treating diseases characterized by abnormal PTKs activity of erbB family, in particular tumors in mammals, comprising applying, particularly by oral administration, a pharmacologically effective amount of the pharmaceutical composition or formulation of the invention to individual patients.

As used herein, "a pharmaceutical composition" is a form of co-presence of the active ingredient and the stabilizer and an optional carrier or diluent. It should be specified that "a pharmaceutical composition" is not limited to a certain physical state or form.

As used herein, "diseases characterized by abnormal PTKs activity of erbB family" or "diseases characterized by abnormal proliferation caused by abnormal PTKs activity of erbB family" include recognized diseases in the art, such as psoriasis, rheumatoid arthritis, bronchitis, and cancers. It should be specified that the types of the diseases are not limited to these diseases. "Tyrosine kinase mediated" diseases and disorders such as angiogenesis, atherosclerosis, age-related macular degeneration, diabetic retinopathy and the like are all covered by "diseases characterized by abnormal PTKs activity of erbB family" or "diseases characterized by abnormal proliferation caused by abnormal PTKs activity of erbB family" according to the invention.

As used herein, "tumors" and "cancers" mean the same.

As used herein, the term "a pharmacologically effective amount", meaning the same as "a therapeutically effective amount", refers to an amount of the active compound which is sufficient to ameliorate the condition and during administration does not produce a seriously side effect. In this invention, the amount refers to the dose of the active compound which brings about a desired pharmacological response when the pharmaceutical composition or formulation of the invention is administered to a great majority of patients in need of treatment by PTKs inhibitors. It should be understood that under a particular circumstance, such dose may represent an oral dose; under another particular circumstance, such dose is a drug level measured in patients' blood. It needs to be explained that in case of specific individuals or experimental subjects to be treated, even if a dose is considered by one of skill in the art "a therapeutically effective amount", the dose may not always be effective in treatment of those diseases mentioned herein in particular individuals. This is associated with individual particularity and differences of individuals including differences of species and races as well as differences between individuals of the same race.

As used herein, "an active ingredient", "an active compound" and "a pharmacologically active ingredient" mean the same and refer to the quinazoline derivative according to the present invention "pharmaceutically acceptable salts of N-{4-[3-chloro-4-(3-fluoro-benzyloxy)phenylamino]quinazolin-6-yl}-acrylamide", which includes different crystalline forms, different isomers and hydrates thereof, etc., unless specifically stated otherwise.

The pharmaceutically acceptable salts of N-{4-[3-chloro-4-(3-fluoro-benzyloxy)phenylamino]quinazolin-6-yl}-acrylamide, as stated in the aforesaid application document PCT/CN2008/000318, include but not limited to salts formed by N-{4-[3-chloro-4-(3-fluoro-benzyloxy)phenylamino]quinazolin-6-yl}-acrylamide with the following acids: hydrochloric acid, hydrobromic acid, hydroiodic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethanesulfonic acid, toluenesulfonic acid, benzenesulfonic acid or isethionic acid. Other salts include amine salts, alkali metal or alkaline earth metal (e.g., sodium, potassium, calcium or magnesium) salts of N-{4-[3-chloro-4-(3-fluoro-benzyloxy)phenylamino]quinazolin-6-yl}-acrylamide, preferably toluenesulfonate, hydrochloride, tartrate, sulfate, oxalate, and triethylamine salts of N-{4-[3-chloro-4-(3-fluoro-benzyloxy)phenylamino]quinazolin-6-yl}-acrylamide, particularly preferably N-{4-[3-chloro-4-(3-fluoro-benzyloxy)phenylamino]quinazolin-6-yl}-acrylamide p-toluenesulfonate.

P-toluenesulfonate of N-{4-[3-chloro-4-(3-fluoro-benzyloxy)phenylamino]quinazolin-6-yl}-acrylamide has superior physico-chemical properties than the salt-forming compound itself. For instance, in terms of moisture absorbency, the salt merely absorb a minor amount of moisture even exposed in a wide range of humidity. Moreover, the compound may be present in stable crystalline forms, thus being more suitable as medicament. The applicant gives a detailed account of the crystalline forms (crystalline forms A, B and C) of p-toluenesulfonate of N-{4-[3-chloro-4-(3-fluoro-benzyloxy)phenylamino]quinazolin-6-yl}-acrylamide in the Chinese patent application CN 200810043189.7 filed on Mar. 25, 2008. This application is fully incorporated herein by reference.

The three crystalline forms of p-toluenesulfonate of N-{4-[3-chloro-4-(3-fluoro-benzyloxy)phenylamino]quinazolin-6-yl}-acrylamide may be used alone or in combination for the preparation of the pharmaceutical composition of the present invention.

The stabilizer of the present invention, which has dispersing and/or protective effect on the active ingredient, is mainly selected from high-molecular substances and surfactant substances, such as, one or more substances selected from the group consisting of hydroxypropyl methyl cellulose, hydroxypropyl cellulose, calcium carboxymethyl cellulose, sodium carboxymethyl cellulose, methyl cellulose, hydroxyethyl cellulose, povidone, sodium dodecylsulphonate, amylum pregelatinisatum, microcrystalline cellulose, polyethylene glycols, dioctyl sulfosuccinate, gelatin, arabic gum, tragacanth, stearic acid, calcium stearate, lecithin, dextran, cholesterol, glycerol monostearate, sorbitan esters, polyoxyethylene alkyl ethers, polyoxyethylene castor oil derivatives, polyoxyethylene sorbitan fatty acid esters, polyoxyethylene stearate, polyvinyl alcohol, poloxamers, colloidal silicon dioxide, magnesium aluminum silicate, alginate, chitosan, and polylysine; preferably compressible starch, hydroxypropyl methyl cellulose, hydroxypropyl cellulose, sodium carboxymethyl cellulose, polyethylene glycols, arabic gum, gelatin, polyoxyethylene sorbitan fatty acid esters, colloidal silicon dioxide, poloxamers, chitosan, polyoxyethylene castor oil derivatives, and microcrystalline cellulose; particularly preferably compressible starch, sodium carboxymethyl cellulose, arabic gum, and poloxamers.

The ratio by weight of the stabilizer to the active ingredient is 1:0.1 to 10, preferably 1:0.1 to 5, and particularly preferably 1:0.2 to 2.

In the pharmaceutical composition of the present invention, the pharmaceutically acceptable salt of N-{4-[3-chloro-4-(3-fluoro-benzyloxy)phenylamino]quinazolin-6-yl}-acrylamide as the active ingredient comprises about from 0.1% to 90% of the total weight of the composition.

In the preparation of the pharmaceutical composition of the present invention, typically, the active ingredient is fully mixed with the stabilizer so that the stabilizer plays the role of dispersion and/or protection. Subsequently the resultant mixture is mixed with an optional (i.e., non-compulsory) pharmaceutically applicable carrier or diluent.

In the specific formulations formulated using the pharmaceutical composition of the invention, the type of the stabilizer may be the same as carriers (auxiliary materials) for other uses in the formulation. For example, non-limiting example, a tablet comprising the active ingredient of the present invention comprises compressible starch, wherein a portion of the compressible starch, as the stabilizer, is mixed with the active ingredient, and the rest of the compressible starch is for its conventional use, acting as, for example, a filler, a disintegrant, and a dried binder.

The pharmaceutical composition of the invention has good capability for formulation and good stability as well as high bioavailability.

When the stabilizer of the present invention is used, the composition of the present invention may be formulated by a conventional preparation method into a conventional pharmaceutical formulation such as tablets, pills, capsules, powders, granules, emulsions, suspensions, solutions, syrups, elixirs, injections, suppositories, patches using a pharmaceutically applicable carrier or diluent.

In the pharmaceutical formulation formulated using the composition of the invention, the weight ratio of the stabilizer to the active ingredient is 1:0.1 to 10, preferably 1:0.1 to 5, and particularly preferably 1:0.2 to 2.

The pharmaceutically acceptable salt of N-{-4-[3-chloro-4-(3-fluoro-benzyloxy)phenylamino]quinazolin-6-yl}-acrylamide as the active ingredient comprises from 0.1 to 90%, preferably from 0.1 to 70% of the total weight of the pharmaceutical formulation formulated using the composition of the invention.

The pharmaceutical composition of the invention may be formulated into a liquid formulation, wherein the pharmaceutically acceptable salt of N-{4-[3-chloro-4-(3-fluoro-benzyloxy)phenylamino]quinazolin-6-yl}-acrylamide is present in an amount of from 0.1% to 50% by weight, based on the total weight of the formulation, wherein the carrier includes one or more of the following substances: a solvent, a pH regulator, an isotonic regulator, a flavoring agent, an odor-masking agent, a colorant, a preservative, and an antioxidant, wherein the weight ratio of the stabilizer to the active ingredient is 1:0.1 to 5, preferably 1:0.1 to 2, and particularly preferably 1:0.2 to 2. The liquid formulation may be an oral formulation.

The solvent may be one or more selected from the group consisting of water, glycerol, propanediol, polyethylene glycols, $C_1$ to $C_6$ fatty alcohols, and fatty oils. The pharmaceutical composition may be formulated into a liquid dosage form for oral administration, including such as, suspensions, solutions, syrups, elixirs and the like. A high-molecular substance having surface activity, or which can disperse in a liquid (as a solvent) to a homogeneous or heterogeneous liquid, is usually selected as the stabilizer, such as sodium dodecyl sulphonate, polyethylene glycols, dioctyl sulfosuccinate, gelatin, arabic gum, tragacanth, lecithin, dextran, cholesterol, glycerol monostearate, sorbitan esters, polyoxyethylene alkyl ethers, polyoxyethylene castor oil derivatives, polyoxyethylene sorbitan fatty acid esters, polyoxyethylene stearate, polyvinyl alcohol, poloxamers, chitosan, polylysine, and the like. Solvents to be selected are, for example, physiologically acceptable solvents: distilled water, physiological saline, ethanol solution in a physiologically acceptable concentration etc. The weight ratio of the stabilizer to the active ingredient is preferably 1:0.1 to 10, especially preferably 1:0.1 to 5, and particularly preferably 1:0.2 to 2.

In an embodiment of the oral liquid formulation of the present invention, the weight percentage of the pharmacologically active ingredient, the pharmaceutically acceptable salt of N-{4-[3-chloro-4-(3-fluoro-benzyloxy)phenylamino]quinazolin-6-yl}-acrylamide in the formulation is preferably from 0.1% to 50%, further preferably from 0.5% to 30%, more preferably from 0.5% to 20%. The ratio by weight of the stabilizer to the active ingredient is preferably 1:0.1 to 5, and more preferably 1:0.2 to 2.

In another embodiment of the oral liquid form of the pharmaceutical formulation of the present invention, based on the weight of the formulation, the pharmaceutically acceptable salts of N-{4-[3-chloro-4-(3-fluoro-benzyloxy)phenylamino]quinazolin-6-yl}-acrylamide is present in an amount of from 0.5% to 20% by weight; the stabilizer is present in an amount of from 2.5% to 30% by weight; the preservative is present in an amount of from 0.1% to 10% by weight; the antioxidant is present in an amount of from 0.1% to 10% by weight; and the solvent is present in an amount of from 30% to 90% by weight.

In one of the embodiments above, the stabilizer is poloxamer 188, and the other carriers include sodium sulfite as an antioxidant, ethyl para-hydroxybenzoate as a preservative, and glycerol and distilled water as a solvent.

In the preparation of the liquid formulation, first, the stabilizer is mixed with the active ingredient. Subsequently, a solvent in a small amount is added and mixed. After the uniform mixture is obtained, a formulation is prepared by a conventional method.

The pharmaceutical composition may also be formulated into an oral solid formulation for oral administration, including such as, tablets, capsules, powders, granules, pills and dry suspensions which may be administrated orally, and the following substances are usually selected as the stabilizer: hydroxypropyl methyl cellulose, hydroxypropyl cellulose, calcium carboxymethyl cellulose, sodium carboxymethyl cellulose, methyl cellulose, hydroxyethyl cellulose, povidone, compressible starch, microcrystalline cellulose, polyethylene glycols, dioctyl sulfosuccinate, gelatin, arabic gum, tragacanth, stearic acid, calcium stearate, lecithin, dextran, cholesterol, glycerol monostearate, polyoxyethylene sorbitan fatty acid esters, polyoxyethylene stearate, polyvinyl alcohol, poloxamers, colloidal silicon dioxide, magnesium aluminum silicate, alginate, chitosan, polylysine and the like. The weight ratio of the stabilizer to the active ingredient is preferably 1:0.1 to 10, especially 1:0.5 to 5, particularly preferably 1:0.5 to 2. In the preparation of an oral solid formulation, the active ingredient and the stabilizer are firstly uniformly mixed and subsequently mixed with other carriers or diluents.

In the preparation of an oral solid formulation, the composition of the invention further comprises a pharmaceutically acceptable carrier or diluent. The carrier includes one or more of the following: a filler, a disintegrant, a wetting agent, a binder, a lubricant, a flavoring agent, odor-masking agent, and a colorant. Said filler is one or more selected from the group consisting of starch, dextrin, sucrose, lactose, fructose, glucose, xylitol, mannitol, calcium carbonate, magnesium carbonate, calcium phosphate, calcium hydrogen phosphate, calcium sulphate, magnesium oxide, and aluminum hydroxide. The disintegrant may be one or more selected from the group consisting of starch, sodium carboxymethyl starch, hydroxypropyl starch, cross-linked sodium carboxymethylcellulose, cross-linked polyvinylpyrrolidone, hydroxypropylmethyl cellulose, as well as an effervescent disintegrant such as a mixture formed from sodium hydrogen carbonate and citric acid. The wetting agent may be selected from distilled water, ethanol, or combination thereof. The binder may be one or more selected from the group consisting of hydroxypropyl methylcellulose, polyvinylpyrrolidone, starch slurry, dextrin, glucose and molasses thereof, sucrose and molasses thereof, lactose and molasses thereof, fructose and molasses thereof, sorbitol, gelatin mucilage, arabic mucilage, tragacanth mucilage, microcrystalline cellulose, methyl cellulose, sodium carboxymethylcellulose, ethyl cellulose, hydroxypropyl cellulose, and hydroxyethyl cellulose. The lubricant may be one or more selected from the group consisting of stearic acid, calcium stearate, magnesium stearate, zinc stearate, talc, glyceryl monostearate, glyceryl palmitostearate, magnesium dodecyl sulfate, PEG4000, PEG6000, and sodium stearyl fumarate. Certainly the carriers are not limited to these types. Any additive commonly used in the preparation of a solid pharmaceutical composition can be included in the oral solid composition of the present invention, as long as it is suitable to the properties of the active ingredient and the particular formulation process.

Preferably, in the oral solid formulations, the active ingredient is present in an amount of 1% to 50% by weight, further preferably 5% to 50% by weight, more preferably 10% to 30% by weight, based on the total weight of the solid formulation. The weight ratio of the stabilizer to the active ingredient is 1:0.5 to 10, preferably 1:0.5 to 5, more preferably 1:0.5 to 2. In an embodiment of the pharmaceutical formulation of the present invention in the form of tablets, the stabilizer is selected to be compressible starch and the rest of the carrier materials include compressible starch and microcrystalline cellulose as a filler; crosslinked polyvinylpyrrolidone as a disintegrant; and stearic acid and/or talc as a lubricant. More specifically, the pharmaceutical formulation in the form of a tablet comprises, based on the weight of the formulation, the pharmaceutically acceptable salt of N-{4-[3-chloro-4-(3-fluoro-benzyloxy)phenylamino]quinazolin-6-yl}-acrylamide in an amount of from 10% to 30% by weight, the compressible starch as stabilizer in an amount of from 5% to 60% by weight, and the rest of the carriers in the formulation are: the filler compressible starch in an amount of from 10% to 50% by weight, microcrystalline cellulose in an amount of from 5% to 60% by weight, crosslinked polyvinylpyrrolidone in an amount of from 2% to 15% by weight, stearic acid in an amount of from 0% to 10% by weight, and talc in an amount of from 0% to 5% by weight, based on the weight of the formulation.

In another embodiment of the pharmaceutical formulation of the present invention in the form of tablets, the stabilizer is selected to be poloxamer 188, and the other carriers include:

microcrystalline cellulose as a filler; crosslinked sodium carboxymethylcellulose as a disintegrant; and magnesium stearate as a lubricant. More specifically, the formulation comprises, from 5% to 15% by weight of the pharmaceutically acceptable salt of N-{-4-[3-chloro-4-(3-fluoro-benzyloxy) phenylamino]quinazolin-6-yl}-acrylamide, from 2.5% to 50% by weight of poloxamer 188, from 2% to 60% by weight of microcrystalline cellulose, from 5% to 25% by weight of crosslinked sodium carboxymethylcellulose, and from 3% to 10% by weight of magnesium stearate, based on the weight of the formulation. The pharmaceutical composition may also be formulated to formulations for administration by other approaches, such as a liquid formulation not for oral administration, for example, those for injection, such as intravenous injection, intramuscular injection or intratumor injection, and the stabilizer having surface activity is selected, such as arabic gum, tragacanth, lecithin, dextran, cholesterol, glycerol monostearate, sorbitan esters, polyoxyethylene alkyl ethers, polyoxyethylene castor oil derivatives, polyoxyethylene sorbitan fatty acid esters, polyoxyethylene stearate, polyvinyl alcohol, poloxamers, alginate and the like. Applicable carriers or diluents include water for injection, physiological saline, physiologically acceptable nontoxic non-volatile oils. The active ingredient may be present in an amount of from 0.1% to 90% by weight, preferably from 0.1% to 50% by weight, particularly preferably from 0.5% to 30% by weight, based on the weight of the formulation.

The pharmaceutical formulation may be formulated as a dosage form for topical administration, such as a lotion, a cream, and a gel, etc. A suppository, administered to the rectum or other cavities, may be prepared by mixing the active ingredient with suitable nonirritant excipients such as cocoa butter or polyethylene glycols. The excipients are solid at room temperature and melted to a liquid within intestine thereby releasing the active ingredient to the rectum.

For convenience of preparation and administration, the preferred pharmaceutical composition is a composition at a solid state, in particular tablets, and capsules filled with solids. For convenience of administration, oral administration is preferred. In order to facilitate use by severe patients, to improve bioavailability and to accelerate drug absorption, the preferred pharmaceutical composition is a liquid formulation including an injection and an oral liquid formulation. Further preferred pharmaceutical composition is an oral liquid formulation. An oral liquid formulation comprising the pharmaceutically acceptable salt of N-{4-[3-chloro-4-(3-fluoro-benzyloxy)phenylamino]quinazolin-6-yl}-acrylamide and the stabilizer according to the present invention has both good stability and homogeneity.

The pharmaceutical composition of the present invention may be formulated in combination with other anti-cancer pharmacologically active ingredients into medicaments for the treatment of cancer. The other anti-cancer pharmacologically active ingredients include cis-platinum, 5-FU, vincristine, taxol, and antitumor antibiotics, etc.

The pharmaceutical formulation of the present invention in a unit form comprises from 10 mg to 1,000 mg by weight of active ingredient. Further, the composition or formulation comprises 10 mg, 30 mg, 40 mg, 50 mg, 100 mg, 200 mg, 300 mg, 400 mg, 500 mg or 1,000 mg by weight of the pharmacologically active ingredient.

Medicinal Use

The pharmaceutical composition of the present invention is useful for inhibiting, regulating and/or controlling signal transduction of tyrosine kinases of erbB family. Specifically, the pharmaceutical composition of the invention is useful in the treatment of the diseases characterized by abnormal PTKs activity of erbB family in mammals, comprising administering to a mammal the pharmaceutical composition comprising a pharmacologically effective amount of the pharmaceutically acceptable salt of N-{4-[3-chloro-4-(3-fluoro-benzyloxy)phenylamino]quinazolin-6-yl}-acrylamide.

The diseases characterized by abnormal PTKs activity of erbB family, as used herein, include the diseases well-known in the art such as psoriasis, rheumatoid arthritis, bronchitis, cancer, angiogenesis, atherosclerosis, age-related macular degeneration, diabetic retinopathy and the like; mammalian tumors including breast cancer, non-small cell cancers, ovarian cancer, gastric cancer, colon cancer, pancreatic cancer and epidermoid squamous cancer, in particular lung cancer, ovarian cancer and breast cancer having high expression of erbB-2.

The pharmaceutical composition of the present invention may be used in combination with other drugs in the treatment of tumors characterized by abnormal PTKs activity of erbB family, such as in combination with cis-platinum, 5-FU, vincristine, taxol, and antitumor antibiotics, etc.

The effective dosage of the pharmaceutically acceptable salts of quinazoline derivative N-{-4-[3-chloro-4-(3-fluoro-benzyloxy)phenylamino]quinazolin-6-yl}-acrylamide having PTKs inhibitory activity according to the present invention may vary with the administration approaches and severity of the diseases to be treated. It has been found by studies that a daily dosage of from 0.5 mg to 2,000 mg of the active compound administered to individuals brings about satisfactory results, even better a divided daily dosage for 2 to 4 times, or administered by sustained-release form. For the majority of large mammals, the total daily dosage is about from 5 mg to 2,000 mg. A suitable oral daily dosage is from 100 mg to 2,000 mg, and from 5 mg to 2,000 mg for a non-oral daily dosage. Naturally, this dosage regime is subjected to regulation depending on individual circumstances so as to provide an optimal therapeutic response.

The pharmaceutical composition of the invention has good capability for formulation and physical and chemical stability. It is convenient for oral administration, of excellent bioavailability and is very suitable for clinical treatment. Pharmacological experiments have shown that the composition has outstanding tumor inhibition effect, low toxic and side effect and more safety when used for treating diseases characterized by abnormal PTKs activity of erbB family, such as, treating mammalian tumors.

Embodiments

The present invention is further described by the following examples. It should be understood that these examples are intended to illustrate the present invention but not to limit the scope thereof. For the experimental methods in the following examples for which the specific conditions are not indicated, the conventional conditions or the conditions suggested by the manufacturers are followed.

(I) PREPARATION OF THE COMPOUNDS

Example 1

Preparation of N-{4-[3-chloro-4-(3-fluoro-benzyloxy)phenylamino]quinazolin-6-yl}-acrylamide Step A: Preparation of 4-[3-chloro-4-(3-fluoro-benzyloxy)phenylamino]-6-nitro-quinazoline 1.20 g (5.7 mmol) of 4-chloro-6-nitro-quinazoline (prepared by referring to WO 2007/082434) and 1.37 g (5.6 mmol) of 4-(3-fluoro-benzyloxy)-3-chloro-aniline (prepared by referring to WO 2007/082434) were dissolved in 80 mL of isopropanol and refluxed for 3 hours. A large amount of yellow solid was precipitated from the system, and was filtered. The filter cake was washed with a saturated sodium bicarbonate aqueous solution till pH=8 and dried under vacuum to give 1.62 g (3.75 mmol) of yellow solid, which was identified as 4-[3-chloro-4-(3-fluoro-benzyloxy)phenylamino]-6-nitro-quinazoline with a yield of 67%.

$^1$H-NMR (400 MHz, CDCl$_3$): δ 11.30(1H, br), 9.54-9.48 (1H, m), 8.45-8.41(1H, m), 8.31-8.25(1H, m), 7.98-7.89(1H, m), 7.50-7.47(1H, m), 7.35-7.26 (1H, m), 7.05-6.96(1H, m), 6.90-6.80(2H, m), 7.74-7.60(2H, m), 4.84(2H, s).

Step B: Preparation of 4-[3-chloro-4-(3-fluoro-benzyloxy)phenylamino]-6-amino-quinazoline To a flask equipped with a refluxing condenser, 1.60 g (3.77 mmol) of the compound 4-[3-chloro-4-(3-fluoro-benzyloxy)phenylamino]-6-nitro-quinazoline prepared according to Step A, 1.05 g (18.85 mmol, 5 eq) of reduced Fe powders, 2 mL of glacial acetic acid and 40 mL of methanol were added and refluxed for 2.5 hours in an oil-bath at a temperature of 85□. The Fe powders were removed by filtration. The filtrate was diluted with ethyl acetate and washed sequentially with sodium bicarbonate solution and water. The organic phase was dried and concentrated to give 900 mg (2.28 mmol) of a yellow solid, which compound was identified as 4-[3-chloro-4-(3-fluoro-benzyloxy)phenylamino]-6-amino-quinazoline with a yield of 61%.

$^1$H-NMR (400 MHz, DMSO): δ 9.32(1H, s), 8.31(1H, s), 8.04(1H, d, J=2.64 Hz), 7.73(1H, dd, J=2.64 Hz, 8.80 Hz), 7.54-7.43(2H, m), 7.36-7.28(3H, m), 7.26-7.14(3H, m), 5.57 (2H, br), 5.27(2H, s).

Step C: Preparation of N-{4-[3-chloro-4-(3-fluorobenzyloxy)-phenylamino]-quinazolin-6-yl}-acrylamide To a flask cooled with an ice-bath, 1.2 g (3.04 mmol) of 4-[3-chloro-4-(3-fluoro-benzyloxy)phenylamino]-6-amino-quinazoline prepared according to Step B, 0.6 mL (4.58 mmol, 1.5 eq) of triethylamine, 0.28 mL (3.33 mmol, 1.1 eq) of acryloyl chloride and 40 mL of THF were added. The reaction temperature rose to room temperature slowly. Three hours later, the reaction was stopped. The resultant mixture was filtered, and the filter cake was washed with water to neutral and dried to give 1.0 g (2.23 mmol) of a yellow solid, which compound was identified as N-{4-[3-chloro-4-(3-fluoro-benzyloxy)phenylamino]-quinazolin-6-yl}-acrylamide with a yield of 67%. MS: 449. mp: 222-225□.

$^1$H-NMR (400 MHz, CDCl$_3$+DMSO): δ 8.75(1H, s), 8.60-8.52(2H, m), 7.81(1H, d, J=2.44 Hz), 7.69(2H, s), 7.54(1H, dd, J=2.56 Hz, 8.92 Hz), 7.30-7.22(2H, m), 7.18-7.08(2H, m), 6.96-6.86(2H, m), 6.37(2H, d, J=5.86 Hz), 5.67(1H, t, J=5.86 Hz), 5.06(2H, s).

Example 2

Preparation of Crystalline Form a of p-Toluenesulfonate of N-{4-[3-chloro-4-(3-fluoro-benzyloxy) phenylamino]quinazolin-6-yl}-a crylamide 3 g (6.68 mmol) of the compound N-{4-[3-chloro-4-(3-fluoro-benzyloxy)phenylamino]-quinazolin-6-yl}-acrylamide prepared according to the method of Example 1 was dissolved in the mixture of tetrahydrofuran and methanol (THF/CH$_3$OH=1/1, 50 mL), and a 38 mL solution of p-toluenesulfonic acid (6 eq, 7.62 g) in the mixture of tetrahydrofuran and methanol (THF/CH$_3$OH=1/1) was added dropwise into the system slowly, and then a large amount of yellow green solid was slowly precipitated from the system during the addition. The solid was filtered, and the filter cake was washed with water and dried under vacuum to give 2.93 g of the title compound as yellow green crystalline powders with a yield of 70%. Melting point: 245° C.

The X-ray powder diffraction measurement (RIGAKUD/MNX2550VB/PC X ray diffractometer): high intensity peaks are identified at the diffraction angle 2θ(°) of the values 5.92±0.10, 8.64±0.10, 11.86±0.10, 16.58±0.10, 16.94±0.10, 17.86±0.10, 19.12±0.10, 19.66±0.10, 20.12±0.10, 23.42±0.10, 24.14±0.10, 24.80±0.10, 26.76±0.10.

Example 3

Preparation of Crystalline Form B of p-Toluenesulfonate of N-{-4-[3-chloro-4-(3-fluoro-benzyloxy) phenylamino]quinazolin-6-yl}-a crylamide 3 g (4.84 mmol) of crystalline form A of p-Toluenesulfonate of N-{4-[3-chloro-4-(3-fluoro-benzyloxy)phenylamino]-quinazolin-6-yl}-acrylamide prepared according to the method of Example 2 was added to the mixture of tetrahydrofuran and water (THF/H$_2$O=4/1, 70 mL), and the resultant mixture was slowly risen to a temperature of 65□ which was continuously kept for 20 min and then cooled to the room temperature slowly, and then stood still at 2□ for 16 h. The resultant mixture was filtered, and the filter cake was washed with water and dried under vacuum to give 1.68 g of the title compound as pale yellow crystalline powders with a yield of 56%. Melting point: 235.4° C.

The X-ray powder diffraction measurement (RIGAKUD/MNX2550VB/PC X ray diffractometer): high intensity peaks are identified at the diffraction angle 2θ (°) of the values 4.72±0.10, 17.04±0.10, 19.32±0.10, 24.12±0.10.

Example 4

Preparation of Crystalline Form C of p-Toluenesulfonate of N-{-4-[3-chloro-4-(3-fluoro-benzyloxy) phenylamino]quinazolin-6-yl}-a crylamide 3 g (4.84 mmol) of crystalline form A of p-Toluenesulfonate of N-{-4-[3-chloro-4-(3-fluoro-benzyloxy)phenylamino]-quinazolin-6-yl}-acrylamide prepared according to the method of Example 2 or 3 was added to the mixture of tetrahydrofuran and water (THF/H$_2$O=3/1, 60 mL). To the system, a 38 mL solution of p-toluenesulfonic acid (6 eq, 7.62 g) in the mixture of tetrahydrofuran and methanol (THF/CH$_3$OH=2/1) was added dropwise slowly, and then a large amount of yellow solid was slowly precipitated from the system during the addition. The solid was filtered, and the filter cake was washed with water and dried under vacuum to give 2.85 g of the title compound as yellow crystalline powders with a yield of 95%. Melting point: 244° C.

The X-ray powder diffraction measurement (RIGAKUD/MNX2550VB/PC X ray diffractometer): high intensity peaks are identified at the diffraction angle 2θ (°) of the values 3.40±0.10, 6.82±0.10, 7.58±0.10, 11.30±0.10, 14.84±0.10, 15.24±0.10, 17.28±0.10, 17.86±0.10, 18.34±0.10, 20.32±0.10, 22.96±0.10, 23.50±0.10, 24.12±0.10, 24.62±0.10, 25.86±0.10.

(II) Studies of Pharmacological Effects

The inventor studied mammalian absorption in vivo and pharmacological effects of the series of compounds, using p-toluenesulfonate of N-{4-[3-chloro-4-(3-fluoro-benzyloxy)phenylamino]quinazolin-6-yl}-acrylamide as a model drug. See the following examples for details.

Example 5

Test on the Drug Absorption in SD Rat (Sprague Dawley Rat)

Intragastric administration (ig): 16 healthy SD rats (Shanghai Super-B&K Laboratory Animal Corp. Ltd., grade SPF), male, weighted 200-250 g, randomly divided into four groups, were each administered intragastrically with a drug: the compound prepared according to Example 1 (21.68 mg/kg), crystalline form A, crystalline form B, or crystalline form C (30 mg/kg) of p-toluenesulfonate of said compound. The blood samples were collected at 0.5 h, 1.0 h, 1.5 h, 2.0 h, 3.0 h, 5.0 h, 7.0 h, 9.0 h, 12 h, and 24 h after administration, which were then isolated to prepare the plasma. The concentrations of the drugs in the plasma were determined by means of liquid phase chromatography/tandem mass spectrometer (Agilent 1200LC/6410B), and the concentration-time curve was obtained.

The main pharmacokinetic parameters are shown in Table 1:

TABLE 1

Experimental results of absorption by ig

| | Dosage (mg/kg) | $T_{max}$ (h) | $C_{max}$ (ng/mL) | $AUC_{0-t}$ (ng · h/mL) | $T_{1/2}$ (h) |
|---|---|---|---|---|---|
| The compound of Example 1 | 21.68 | 0.75 | 32 | 106 | 1.81 |
| Crystalline form A | 30 | 2.83 | 187 | 977 | 1.49 |
| Crystalline form B | 30 | 1.25 | 253 | 978 | 1.23 |
| Crystalline form C | 30 | 2.25 | 161 | 577 | 1.27 |

Intravenous injection (iv): 4 healthy SD rats, male, weighted 200-250 g, were intravenously administered with p-toluenesulfonate of the compound of Example 1 (5 mg/kg). The blood samples were collected at 5 min, 15 min, 0.5 h, 1.5 h, 2.0 h, 3.0 h, 4.0 h, 5.0 h and 7.0 h after administration, which were then isolated to prepare the plasma. The concentrations of the drugs in the plasma were determined by means of liquid phase chromatography/tandem mass spectrometer and the concentration-time curve was obtained. The main pharmacokinetic parameters are shown in Table 2:

TABLE 2

Experimental results of absorption by intravenous injection

| Compound | Dosage (mg/kg) | $T_{max}$ (h) | $C_{max}$ (ng/mL) | $AUC_{0-t}$ (ng · h/mL) | $T_{1/2}$ (h) |
|---|---|---|---|---|---|
| p-toluene sulfonate | 5 | 0.083 | 1745 | 1860 | 1.55 |

By calculation of $AUC_{0-t}$ after dosage calibration, the absolute bioavailability of each of the compound of Example 1, crystalline form A, crystalline form B and crystalline form C administered by ig is 0.95%, 8.75%, 8.76%, and 5.17%, respectively.

Example 6

Tumor-Inhibitory Effect on Human Epidermoid Squamous Cancer Cell A431 Grafted to a BALB/cA Nude Mouse A well-developed solid tumor A431 was selected and incised into several uniform pieces with the size of 2-3 mm under sterile conditions, with one piece being grafted subcutaneously to the right armpit of each of the BALB/cA nude mice using a trocar. 7 days after the grafting, the mice were grouped randomly and were intragastrically administrated through mouth for 13 successive days. The long axis (a) and the short axis (b) of the tumors were measured with a vernier caliper every 4 days. According to the formula $V=ab^2/2$, the volume of the tumor (mm$^3$) could be calculated. The tested animals were neck-off killed 23 days after the grafting, and anatomized to obtain the tumors. The tumors were weighed, and the tumor inhibition rate was calculated.

The result was shown in Table 3 below, showing that p-toluenesulfonate of N-{-4-[3-chloro-4-(3-fluoro-benzyloxy)phenylamino]-quinazolin-6-yl}-acrylamide has a significant inhibitory effect on the tumor.

TABLE 3

Tumor-inhibitory effect on human epidermoid squamous cancer A431

| Group | Dosage (mg/kg) | Administration route | Number of animals Start | Number of animals End | Weight of animals (g) (tumor-off) | Weight of tumor (g) $\bar{x}$ ± SD | Tumor-inhibitory rate % |
|---|---|---|---|---|---|---|---|
| Solvent control | 25 mL/kg | ig | 7 | 7 | 22.40 ± 2.81 | 1.13 ± 0.18 | 0 |
| Crystalline form A | 25 | ig | 5 | 5 | 21.58 ± 2.18 | 0.79 ± 0.20 | 29.99 |
| | 50 | ig | 5 | 5 | 22.87 ± 3.96 | 0.69 ± 0.17 | 38.67 |
| | 100 | ig | 5 | 5 | 22.13 ± 1.83 | 0.64 ± 0.23 | 43.63 |

Example 7

Tumor-Inhibitory Effect on Human Ovarian Cancer SKOV-3 Grafted to a BALB/cA Nude Mouse A SKOV-3 tumor tissue in vigorous growth period was selected and incised into uniform pieces with the size of about 1.5 mm$^3$, which was grafted subcutaneously to the right arm pit of a BALB/cA nude mouse (Shanghai Institute of Materia Medica, Chinese Academy of Sciences, grade SPF) with a trocar under sterile conditions. The diameters of the grafted tumors on the nude mouse were measured with a vernier caliper. The animals were grouped randomly when the tumors grew to a size of 80 to 100 mm³. The tested animal groups were intragastrically administered through mouth as mentioned above once a day for 3 consecutive weeks. The positive control drug MMC (Mitomycin) was intravenously administered once on the first day with a dose of 5 mg/kg (0.9% sterile sodium chloride solution). The negative control group was administered with 0.5% CMC-Na (Carboxymethyl Cellulose-Sodium) with a dose of 0.2 mL/per mouse. The long axis (a) and the short axis (b) of the tumors were measured twice every week and the nude mice were weighed at the same time. According to the formula V=ab²/2, the volume (mm³) of the tumor could be calculated. Relative tumor volume (RTV) was calculated from the measurement result (according to the formula: $RTV=V_t/V_0$, wherein $V_0$ is the tumor volume measured upon the grouping time of administration, and $V_t$ is the tumor volume measured each time). The relative tumor proliferation rate T/C(%) was chosen as the index of evaluation of anti-tumor activity, by the formula:

$$T/C(\%)=(T_{RTV}/C_{RTV})\times100$$

$T_{RTV}$: RTV of the treated group; $C_{RTV}$: RTV of the negative control group The standard for evaluating the effectiveness: T/C(%)>60% means ineffective and T/C(%) ☐60% means effective.

The result was shown in Table 4 below, showing that crystalline form A of p-toluenesulfonate of the compound has a significant inhibitory effect on the tumor.

Example 8

Study of Stability at High Temperature

A small amount of crystalline form A of p-toluenesulfonate of the compound was taken and stored in a high-temperature surroundings of 60° C. for 1 month, the purity of the crystalline form A was detected at day 0, day 10 and day 30, thereby deducing thermal stability of crystalline form A. Thermal stability of crystalline forms B and C were obtained by the same approach. The experimental results are shown in Table 5.

TABLE 5

Experimental results of thermal stability of the p-toluenesulfonate

| | Crystalline form | | | | | | | | |
|---|---|---|---|---|---|---|---|---|---|
| | Crystalline form A | | | Crystalline form B | | | Crystalline form C | | |
| | Detecting time (day) | | | | | | | | |
| | 0 | 10 | 30 | 0 | 10 | 30 | 0 | 10 | 30 |
| Purity (%) | 98.64 | 98.64 | 98.64 | 99.26 | 99.21 | 99.11 | 99.03 | 97.08 | 97.55 |

The above experimental results showed that the purities of crystalline forms A and B almost maintained the same while the purity of crystalline form C slightly dropped when stored in a high-temperature surroundings of 60° C. This demon-

TABLE 4

Tumor-inhibitory effect on human ovarian cancer SKOV-3

| Group | Dosage, Administration route | | Number of test animals | | Volume of tumor (mm³) | | | T/C (%) |
|---|---|---|---|---|---|---|---|---|
| | | | Start | End | $V_0$ | $V_{21}$ | RTV | |
| 0.5% CMC-Na | 0.2 mL//per mouse | ig | 12 | 12 | 85 ± 35 | 638 ± 339 | 9.6 ± 5.4 | |
| MMC | 5 mg/kg | iv | 6 | 6 | 83 ± 13 | 258 ± 77 | 3.1 ± 0.5 | 32.0 |
| Crystalline form A | 200 mg/kg | ig | 6 | 6 | 86 ± 13 | 303 ± 72 | 3.5 ± 0.8 | 36.9 |
| | 100 mg/kg | ig | 6 | 6 | 87 ± 41 | 345 ± 88 | 4.3 ± 1.3 | 45.0 |
| | 50 mg/kg | ig | 6 | 6 | 79 ± 28 | 421 ± 89 | 5.1 ± 1.7 | 53.0 |

$V_0$ denotes the volume of tumor prior to the administration;
$V_{21}$ denotes the volume of tumor after administration for consecutive 3 weeks Human epidermoid squamous carcinoma A431 grafted to BALB/cA nude mouse is an animal model having high expression of EGFR (erbB-1), and human ovarian cancer SKOV-3 grafted to BALB/cA nude mouse is an animal model having high expression of erbB-2. The experimental results have shown that p-toluenesulfonate of N-{-4-[3-chloro-4-(3-fluoro-benzyloxy)phenylamino]quinazolin-6-yl}-acrylamide has a remarkable inhibitory effect on tumor growth of these two models.

(III) Study of Stability

The applicant studied the stability of p-toluenesulfonate of N-{4-[3-chloro-4-(3-fluoro-benzyloxy)phenylamino]quinazolin-6-yl}-acrylamide of the present invention.

strates that crystalline forms A and B of the present invention have excellent thermal stability and crystalline form C has good thermal stability.

Example 9

Study of Light Stability

A small amount of crystalline form A of p-toluenesulfonate of the compound was taken and stored under the environment of illumination with an intensity of 4500lx±500lx for 1 month. The purity of the crystalline form A was detected at day 0, day 10 and day 30, thereby deducing light stability of crystalline form A. The light stability of each of crystalline forms B and C is obtained by the same approach. The experimental results are shown in Table 6.

TABLE 6

Experimental results of light stability of p-toluenesulfonate

| | Crystalline form | | | | | | | | |
|---|---|---|---|---|---|---|---|---|---|
| | Crystalline form A | | | Crystalline form B | | | Crystalline form C | | |
| | Detecting time (day) | | | | | | | | |
| | 0 | 10 | 30 | 0 | 10 | 30 | 0 | 10 | 30 |
| Purity (%) | 98.64 | 98.16 | 97.24 | 99.26 | 99.26 | 99.24 | 99.03 | 98.54 | 98.42 |

The above experimental results indicated that the purity of crystalline form B almost maintained the same while the purities of crystalline forms A and C slightly dropped under the environment of illumination with an intensity of 4500lx±500lx, This demonstrated that crystalline form B of the present invention has excellent light stability, and crystalline forms A and C have good light stability.

The above experimental results show that the purity of the crystalline form B almost maintained the same while the purities of the crystalline forms A and C slightly dropped under the environment of illumination with an intensity of 4500lx±500lx. This demonstrates that the crystalline form B of the invention has excellent light stability and the crystalline forms A and C have good light stability.

Example 10

Study of Hygroscopicity

A small amount of crystalline form A of p-toluenesulfonate of the compound was taken and stored in highly humid surroundings of 92.5% humidity for 1 month, the purity of the crystalline form A was detected at day 0, day 10 and day 30, thereby deducing hygroscopicity of the crystalline form A. Hygroscopicities of the crystalline forms B and C were obtained by the same approach. The experimental results are shown in Table 7.

TABLE 7

Experimental results of hygroscopicity of p-toluenesulfonate

| | Crystalline form | | | | | | | | |
|---|---|---|---|---|---|---|---|---|---|
| | Crystalline form A | | | Crystalline form B | | | Crystalline form C | | |
| | Detecting time (day) | | | | | | | | |
| | 0 | 10 | 30 | 0 | 10 | 30 | 0 | 10 | 30 |
| Purity (%) | 98.64 | 98.62 | 98.62 | 99.26 | 99.25 | 99.24 | 99.03 | 98.27 | 98.08 |

The above experimental results show that purities of the crystalline forms A and B almost maintained the same while the purity of the crystalline form C slightly dropped in the highly humid surroundings of 92.5% humidity. This demonstrates that the crystalline forms A and B of the present invention are very stable and the crystalline form C is quite stable in highly humid surroundings.

The above experimental results show that the crystalline forms of the present invention are quite stable in surroundings with high-temperature, light radiation or high humidity.

(IV) Study of Formulation Adaptability

A pharmaceutical composition applied to patients must have a certain form of formulation. The applicant studied the formulation applicability of the pharmaceutically acceptable salts of N-{4-[3-chloro-4-(3-fluoro-benzyloxy)phenylamino]quinazolin-6-yl}-acrylamide.

The pharmaceutically acceptable salts of N-{4-[3-chloro-4-(3-fluoro-benzyloxy)phenylamino]quinazolin-6-yl}-acrylamide as an active ingredient are difficult to homogenously disperse in a carrier or diluent and prone to re-aggregation at an attainable dispersion extent. Moreover, the crystalline forms of the active ingredient may undergo changes in the presence of a compression process during formulation preparation, for example, a process of squeezing granulation or tabletting.

In the present invention, the applicant provides a pharmaceutical composition comprising a pharmaceutically acceptable salt of N-{4-[3-chloro-4-(3-fluoro-benzyloxy)phenylamino]quinazolin-6-yl}-acrylamide and a stabilizer that has dispersing and/or protective effect on the active ingredient. Addition of the stabilizer surprisingly got benefits from the increase of the dissolution of the pharmaceutically acceptable salt of N-{4-[3-chloro-4-(3-fluoro-benzyloxy)phenylamino]quinazolin-6-yl}-acrylamide in the formulation thereby enhancing bioavailability thereof.

The prescriptions and preparation of formulations of the pharmaceutical composition according to the present invention are further illustrated below. In the prescriptions of the following examples, the pharmaceutically acceptable salt of N-{4-[3-chloro-4-(3-fluoro-benzyloxy)phenylamino]quinazolin-6-yl}-acrylamide is represented by API, and each ingredient in the prescriptions is in gram.

Example 11

Tablets Comprising p-toluenesulfonate of N-{4-[3-chloro-4-(3-fluoro-benzyloxy)phenylamino]quinazolin-6-yl}-acrylamide Comparative Example of Tablet

| Prescription: | |
|---|---|
| API, mixed crystalline forms | 100 |
| amylum pregelatinisatum | 400 |
| Microcrystalline cellulose | 300 |
| Crosslinked sodium carboxymethylcellulose | 150 |
| Stearic acid | 20 |
| Talc | 30 |
| Total weight | 1000 |

Preparation: API was fully mixed with the auxiliary materials in the prescription and compressed into tablets (1,000 tablets).

Examples of Tablets

| Tablet Prescription 1 | |
|---|---|
| API, mixed crystalline forms | 100 |
| amylum pregelatinisatum (A) | 100 |
| amylum pregelatinisatum (B) | 300 |
| Microcrystalline cellulose | 300 |
| Crosslinked sodium carboxymethylcellulose | 150 |
| Stearic acid | 20 |
| Talc | 30 |
| Total weight | 1000 |

Preparation: API was fully mixed with the amylum pregelatinisatum (A) so that API was homogenously dispersed therein, to which the amylum pregelatinisatum (B) and the microcrystalline cellulose were added and fully mixed; the mixture was passed through a 80 mesh sieve, and the rest of the auxiliary materials were added, mixed homogenously, and directly compressed into tablets (1,000 tablets) with rigidity controlled in a range between 60 and 70 N.

| Tablet Prescription 2 | |
|---|---|
| API, crystalline form A | 500 |
| Chitosan | 250 |
| Microcrystalline cellulose | 200 |
| Crosslinked polyvinylpyrrolidone | 20 |
| Stearic acid | 20 |
| Talc | 10 |
| Total weight | 1000 |

Preparation: API was fully mixed with the chitosan so that API was homogenously dispersed therein, to which the rest of the auxiliary materials were added, mixed homogenously, and directly compressed into tablets (1,000 tablets) with rigidity controlled in a range between 60 and 70 N.

| Tablet Prescription 3 | |
|---|---|
| API, crystalline form B | 200 |
| amylum pregelatinisatum | 200 |
| Microcrystalline cellulose | 400 |
| Crosslinked sodium carboxymethylcellulose | 100 |
| Stearic acid | 80 |
| Talc | 20 |
| Total weight | 1000 |

Preparation: API was fully mixed with the amylum pregelatinisatum so that API was homogenously dispersed therein, to which the rest of the auxiliary materials were added, mixed homogenously, and ethanol in a concentration of 70% was added to conduct wet granulation; the result was dried, granulated and compressed into tablets (1,000 tablets) with rigidity controlled in a range between 60 and 70 N.

| Tablet Prescription 4 | |
|---|---|
| API, crystalline form C | 50 |
| Colloidal silicon dioxide | 25 |
| Anhydrous lactose | 600 |
| Crosslinked polyvinylpyrrolidone | 150 |
| Stearic acid | 60 |
| Talc | 40 |
| Total weight | 925 |

Preparation: API was fully mixed with the colloidal silicon dioxide so that API was homogenously dispersed therein, to which the rest of the auxiliary materials were added, mixed homogenously, and directly compressed into tablets (1,000 tablets) with rigidity controlled in a range between 60 and 70 N.

| Tablet Prescription 5 | |
|---|---|
| API, crystalline form B | 250 |
| Poloxamer 188 | 240 |
| Microcrystalline cellulose | 400 |
| Hydroxypropyl methyl cellulose | 10 |
| Stearic acid | 100 |
| Total weight | 1000 |

Preparation: API was fully mixed with the poloxamer 188 so that API was homogenously dispersed therein, to which the rest of the auxiliary materials were added, mixed homogenously, and directly compressed into tablets (1,000 tablets) with rigidity controlled in a range between 60 and 70 N.

All of these obtained tablets were measured in terms of rigidity, content range, disintegration time and dissolution. The dissolution is measured under the following test conditions: dissolution medium: 900 ml of 3% sodium dodecyl sulphonate solution comprising 1.2 mmol/L NaOH; dissolution conditions: 37° C., 100 rpm; measuring the samples at 246 nm with an ultraviolet spectrophotometer (Shimadzu UV-2450); making a standard curve, and calculating the content and dissolution of the sample.

The measurement results of rigidity, disintegration time and dissolution of the tablets prepared from the above-mentioned prescriptions are listed in Table 8 below (all of the dissolution are ones at 45 minutes). It can be seen that the tablets have good capability for formulation.

TABLE 8

Measurement results of rigidity, disintegration time and dissolution of the tablets

| Prescription No. | Rigidity (N) | Percentage range of the labeled amount (%) | Disintegration Time (min) | Dissolution (%) |
|---|---|---|---|---|
| Comparative example | 65 | 93.0-108.2 | 5.8 | 67.4 |
| Prescription 1 | 65 | 99.2-100.2 | 5.2 | 98.5 |
| Prescription 2 | 68 | 98.5-99.9 | 6.1 | 99.6 |
| Prescription 3 | 69 | 98.6-101.1 | 6.4 | 101.2 |
| Prescription 4 | 70 | 99.7-99.8 | 6.4 | 97.5 |
| Prescription 5 | 63 | 98.7-102.1 | 5.6 | 98.6 |

The stability of the tablets prepared from the above-mentioned prescriptions was tested under acceleration conditions and under room temperature by the method stipulated in Chinese Pharmacopoeia. Results of stability tests under acceleration conditions for 3 months and under room temperatures for 3 months are shown below in Table 9. It can been seen that the formulations prepared are stable.

TABLE 9

Test results of tablet stability

| | Acceleration for 3 months | | | | Room temperature for 3 months | | | |
|---|---|---|---|---|---|---|---|---|
| Prescription No. | Rigidity (N) | Percentage range of labeled amount | Disintegration Time (min) | Dissolution (%) | Rigidity (N) | Content range (%) | Disintegration Time (min) | Dissolution (%) |
| Comparative | 65 | 94.3-106.3 | 5.6 | 59.6 | 66 | 93.6-107.9 | 5.5 | 64.6 |
| 1 | 66 | 97.3-98.8 | 6.0 | 99.2 | 65 | 97.4-101.0 | 5.3 | 99.5 |
| 2 | 67 | 97.8-99.8 | 6.5 | 99.8 | 68 | 98.2-99.8 | 6.0 | 99.3 |
| 3 | 70 | 98.5-101.0 | 6.8 | 98.7 | 68 | 99.7-101.1 | 6.5 | 99.2 |
| 4 | 70 | 97.6-100.2 | 7.0 | 98.5 | 69 | 97.8-99.9 | 6.6 | 98.8 |
| 5 | 63 | 98.6-101.2 | 6.0 | 98.6 | 64 | 98.5-100.5 | 6.5 | 97.9 |

Example 12

Tablets comprising N-{4-[3-chloro-4-(3-fluoro-benzyloxy)phenylamino]quinazolin-6-yl}-acrylamide hydrochloride Comparative Example of Tablet

| Prescription: | |
|---|---|
| API | 100 |
| amylum pregelatinisatum | 400 |
| Microcrystalline cellulose | 300 |
| Crosslinked sodium carboxymethylcellulose | 150 |
| Stearic acid | 20 |
| Talc | 30 |
| Total weight | 1000 |

Preparation: API was fully mixed with the auxiliary materials in the prescription and compressed into tablets (1,000 tablets).

Examples of Tablets

| Tablet Prescription 1 | |
|---|---|
| API | 100 |
| Hydroxypropyl cellulose | 100 |
| Microcrystalline cellulose | 300 |
| Spray dried lactose | 300 |
| Crosslinked sodium carboxymethylcellulose | 150 |
| Stearic acid | 20 |
| Talc | 30 |
| Total weight | 1000 |

Preparation: API was fully mixed with the hydroxypropyl cellulose so that API was homogenously dispersed therein; the mixture was passed through a 80 mesh sieve, and the rest of the auxiliary materials were added, mixed homogenously, and directly compressed into tablets (1,000 tablets) with rigidity controlled in a range between 60 and 70 N.

| Tablet Prescription 2 | |
|---|---|
| API | 350 |
| Chitosan | 400 |
| Microcrystalline cellulose | 200 |
| Crosslinked polyvinylpyrrolidone | 20 |
| Stearic acid | 20 |
| Talc | 10 |
| Total weight | 1000 |

Preparation: API was fully mixed with the chitosan so that API was homogenously dispersed therein, to which the rest of the auxiliary materials were added, mixed homogenously, and directly compressed into tablets (1,000 tablets) with rigidity controlled in a range between 60 and 70 N.

The stability of the tablets prepared from the above-mentioned prescriptions was tested under acceleration conditions and under room temperature by the method stipulated in Chinese Pharmacopoeia. Results of stability tests under acceleration conditions for 3 months and under room temperatures for 3 months are shown below in Table 10. It can be seen that the formulations prepared are stable.

TABLE 10

Test results of tablet stability

| | Acceleration for 3 months | | | | Room temperature for 3 months | | | |
|---|---|---|---|---|---|---|---|---|
| Prescription No. | Rigidity (N) | Percentage range of labeled amount | Disintegration Time (min) | Dissolution (%) | Rigidity (N) | Percentage range of labeled amount | Disintegration Time (min) | Dissolution (%) |
| Comparative | 69 | 90.3-96.3 | 7.9 | 70.2 | 68 | 89.6-95.9 | 5.6 | 71.8 |
| 1 | 67 | 97.6-102.5 | 5.2 | 98.9 | 69 | 98.9-102.3 | 5.1 | 98.1 |
| 2 | 65 | 96.9-99.8 | 6.0 | 99.3 | 68 | 97.2-99.4 | 6.1 | 99.6 |

Example 13

Capsules Comprising N-{4-[3-chloro-4-(3-fluoro-benzyloxy)phenylamino]quinazolin-6-yl}-acrylamide p-toluenesulfonate

| Capsule Prescription 1 | |
| --- | --- |
| API, mixed crystalline forms | 30 |
| amylum pregelatinisatum (A) | 50 |
| amylum pregelatinisatum (B) | 350 |
| Microcrystalline cellulose | 400 |
| Crosslinked sodium carboxymethylcellulose | 120 |
| Talc | 50 |
| Total weight | 1000 |

Preparation: API was fully mixed with the amylum pregelatinisatum (A) so that API was homogenously dispersed therein, to which the amylum pregelatinisatum (B) and the microcrystalline cellulose were added and fully mixed; the mixture was passed through a 80 mesh sieve, and the rest of the auxiliary materials were added, mixed homogenously, and ethanol in a concentration of 70% was added to conduct wet granulation; the result was dried, granulated and filled into capsules (1,000 capsules).

| Capsule Prescription 2 | |
| --- | --- |
| API, crystalline form A | 500 |
| Chitosan | 250 |
| Microcrystalline cellulose | 200 |
| Crosslinked polyvinylpyrrolidone | 20 |
| Stearic acid | 20 |
| Talc | 10 |
| Total weight | 1000 |

Preparation: API was fully mixed with the chitosan so that API was homogenously dispersed therein, to which the rest of the auxiliary materials were added, mixed homogenously, and filled into capsules (1,000 capsules).

| Capsule Prescription 3 | |
| --- | --- |
| API, crystalline form B | 200 |
| amylum pregelatinisatum | 200 |
| Microcrystalline cellulose | 400 |
| Crosslinked sodium carboxymethylcellulose | 100 |
| Stearic acid | 80 |
| Talc | 20 |
| Total weight | 1000 |

Preparation: API was fully mixed with amylum pregelatinisatum so that API was homogenously dispersed therein, to which the rest of the auxiliary materials were added, mixed homogenously, and filled into capsules (1,000 capsules).

Active ingredient content uniformity and dissolution of the prepared capsules were measured. The results showed that the content differences were lower than 3%, and the dissolution at 45 minutes were 98.5%, 97.8%, 97.8% and 98.6% respectively.

Example 14

An Oral liquid comprising N-{4-[3-chloro-4-(3-fluoro-benzyloxy)phenylamino]quinazolin-6-yl}-acrylamide p-toluenesulfonate

Comparative Examples of an Oral Liquid

| | |
| --- | --- |
| API, crystalline form B | 500 |
| Sodium sulfite | 10 |
| Saccharin sodium | 7 |
| Ethyl para-hydroxybenzoate | 16 |
| Polyethylene glycol 200 | 1600 |
| Distilled water | balance to 10 L |

Preparation: API was completely comminuted, and to which the polyethylene glycol 200 and 2 L of distilled water were added, dissolved by means of high-speed stirring or by ultrasonic, and the rest of the solid auxiliary materials were added, dissolved by means of stirring, and to which distilled water was again added up to 10 L in volume, mixed homogenously, separately packed (10 mL per bottle), and sterilized.

Examples of Oral Liquids

| Oral Liquid Prescription 1 | |
| --- | --- |
| API, crystalline form A | 50 |
| Lecithin | 500 |
| Tween-80 | 65 |
| Saccharin sodium | 5 |
| Sodium sulfite | 10 |
| Ethyl para-hydroxybenzoate | 16 |
| Polyethylene glycol 400 | 2000 |
| Distilled water | balance to 10 L |

Preparation: API was completely comminuted, mixed homogenously with arabic gum, and to which the polyethylene glycol 400 and 2 L of distilled water were added, dissolved by means of stirring, and the rest of the solid auxiliary materials were added, dissolved by means of stirring, and to which distilled water was again added up to 10 L in volume, mixed homogenously, separately packed (10 mL per bottle), and sterilized.

| Oral Liquid Prescription 2 | |
| --- | --- |
| API, crystalline form B | 500 |
| Tragacanth | 1000 |
| Sodium carboxymethylcellulose | 80 |
| Sodium sulfite | 10 |
| Saccharin sodium | 7 |
| Ethyl para-hydroxybenzoate | 16 |
| Polyethylene glycol 200 | 1600 |
| Distilled water | balance to 10 L |

Preparation: API was completely comminuted, mixed homogenously with the tragacanth and sodium carboxymethylcellulose, and to which the polyethylene glycol 200 and 2 L of distilled water were added, dissolved by means of stirring, and the rest of the solid auxiliary materials were added, dissolved by means of stirring, and to which distilled water was again added up to 10 L in volume, mixed homogenously, separately packed (10 mL per bottle), and sterilized.

| Oral Liquid Prescription 3 | |
| --- | --- |
| API, mixed crystalline forms | 700 |
| Poloxamer 188 | 900 |
| Sodium sulfite | 10 |
| Ethyl para-hydroxybenzoate | 16 |
| Glycerol | 1000 |
| Mint oil | 2 |
| Distilled water | balance to 10 L |

Preparation: API was completely comminuted, mixed homogenously with the poloxamer 188, and to which the glycerol and 2 L of distilled water were added, dissolved by means of stirring, and the rest of the solid auxiliary materials and mint oil were added, dissolved by means of stirring, and to which distilled water was again added up to 10 L in volume, mixed homogenously, separately packed (10 mL per bottle), and sterilized.

The oral liquids prepared from the above-mentioned prescriptions stayed still for 30 days at room temperature and properties thereof are shown in the table below.

| Prescription No. | Day 0 | Day 5 | Day 10 | Day 30 |
| --- | --- | --- | --- | --- |
| Comparative example | Homogenous transparent solution | Solid precipitates | A large amount of solid precipitates | A large amount of solid precipitates |
| Prescription 1 | Homogenous transparent solution | Homogenous transparent solution | Homogenous transparent solution | Homogenous transparent solution |
| Prescription 2 | Homogenous transparent solution | Homogenous transparent solution | Homogenous transparent solution | A small amount of solid precipitates |
| Prescription 3 | Homogenous transparent solution | Homogenous transparent solution | Homogenous transparent solution | Homogenous transparent solution |

The experimental results have shown that the pharmaceutical formulations of the present invention have good stability and high bioavailability.

The applicant has set forth the invention in a complete and detailed manner. All the documents and publications mentioned herein are fully or partially incorporated herein by reference.

Obviously, reading the contents of the present invention, one of skill in the art can make various modifications, amendments and alterations which are not depart from the spirits and scope of the invention. These equivalent forms are still within the scope defined by the claims of the present application.

The invention claimed is:

1. A pharmaceutical composition comprising a pharmaceutically acceptable salt of N-{-4-[3-chloro-4-(3-fluoro-benzyloxy)phenylamino]quinazolin-6-yl}-acrylamide as an active ingredient and optionally a pharmaceutically applicable carrier or diluent, and a stabilizer having a dispersing and/or protective effect on the active ingredient, wherein the ratio by weight of the stabilizer to the active ingredient is 1:0.1 to 10, and the stabilizer is one or more selected from the group consisting of hydroxypropyl methyl cellulose, hydroxypropyl cellulose, calcium carboxymethyl cellulose, sodium carboxymethyl cellulose, methyl cellulose, hydroxyethyl cellulose, povidone, sodium dodecyl sulphonate, amylum pregelatinisatum, microcrystalline cellulose, polyethylene glycols, dioctyl sulfosuccinate, gelatin, arabic gum, tragacanth, stearic acid, calcium stearate, lecithin, dextran, cholesterol, glycerol monostearate, sorbitan esters, polyoxyethylene alkyl ethers, polyoxyethylene castor oil derivatives, polyoxyethylene sorbitan fatty acid esters, polyoxyethylene stearate, polyvinyl alcohol, poloxamers, colloidal silicon dioxide, magnesium aluminum silicate, alginate, chitosan and polylysine, wherein the active ingredient is crystalline form A, crystalline form B, or crystalline form C of N-{4-[3-chloro-4-(3-fluoro-benzyloxy) phenylamino]quinazolin-6-yl}-acrylamide p-toluene sulfonate, or mixtures thereof, and wherein:

high intensity peaks for the crystalline form A in an X-ray powder diffraction measurement are identified at the diffraction angle 2θ(°) with the values 5.92±0.10, 8.64±0.10, 11.86±0.10, 16.58±0.10, 16.94±0.10, 17.86±0.10, 19.12±0.10, 19.66±0.10, 20.12±0.10, 23.42±0.10, 24.14±0.10, 24.80±0.10 and 26.76±0.10;

high intensity peaks for the crystalline form B in an X-ray powder diffraction measurement are identified at the diffraction angle 2θ(°) with the values 4.72±0.10, 17.04±0.10, 19.32±0.10 and 24.12±0.10; and high intensity peaks for the crystalline C in an X-ray powder diffraction measurement are identified at the diffraction angle 2θ(°) with the values 3.40±0.10, 6.82±0.10, 7.58±0.10, 11.30±0.10, 14.84±0.10, 15.24±0.10, 17.28±0.10, 17.86±0.10, 18.34±0.10, 20.32±0.10, 22.96±0.10, 23.50±0.10, 24.12±0.10, 24.62±0.10 and 25.86±0.10, with the proviso that when the pharmaceutical composition is prepared, the stabilizer and the active ingredient are firstly homogenously mixed and subsequently mixed with the pharmaceutically applicable carrier or diluents.

2. The pharmaceutical composition according to claim 1, wherein the pharmaceutically acceptable salt of N-{4-[3-chloro-4-(3-fluoro-benzyloxy)phenylamino]quinazolin-6-yl}-acrylamide as the active ingredient is present in an amount of from 0.1% to 90% by weight, based on the total weight of the pharmaceutical composition.

3. The pharmaceutical composition according to claim 1, wherein the active ingredient is selected from the salts formed by N-{4-[3-chloro-4-(3-fluoro-benzyloxy)phenylamino]quinazolin-6-yl}-acrylamide with the acids selected from the group consisting of hydrochloric acid, hydrobromic acid, sulfuric acid, citric acid, tartaric acid, phosphorous acid, lactic acid, pyruvic acid, acetic acid, succinic acid, oxalic acid, fumaric acid, maleic acid, oxaloacetic acid, methanesulfonic acid, ethanesulfonic acid, toluenesulfonic acid, benzensulfonic acid and isethionic acid.

4. The pharmaceutical composition according to claim 1, wherein the salts of N-{4-[3-chloro-4-(3-fluoro-benzyloxy) phenylamino]quinazolin-6-yl}-acrylamide is selected from the group consisting of amine salts, the alkali metal salts and alkaline earth metal salts.

5. The pharmaceutical composition according to claim 1, wherein the active ingredient is selected from the group consisting of toluenesulfonate, hydrochloride, tartrate, sulfate, oxalate, and triethylamine salts of N-{4[3-chloro-4-(3-fluoro-benzyloxy)phenylamino]quinazolin-6-yl}-acrylamide.

6. The pharmaceutical composition according to claim 1, wherein the stabilizer, which has dispersing and/or protective effect on the active ingredient is one or more selected from the group consisting of amylum pregelatinisatum, hydroxypropyl methyl cellulose, hydroxypropyl cellulose, sodium carboxymethyl cellulose, polyethylene glycols, gelatin, arabic gum, polyoxyethylene sorbitan fatty acid esters, poloxamers, colloidal silicon dioxide, chitosan, polyoxyethylene castor oil derivatives and microcrystalline cellulose.

7. The pharmaceutical composition according to claim 1, wherein the stabilizer, which has dispersing and/or protective effect on the active ingredient is one or more selected from the group consisting of amylum pregelatinisatum, sodium carboxymethyl cellulose, arabic gum and poloxamers.

8. The pharmaceutical composition according to claim 1, wherein the active ingredient is N-{4[3-chloro-4-(3-fluoro-benzyloxy)phenylamino]quinazolin-6-yl}-acrylamide p-toluenesulfonate.

9. The pharmaceutical composition according to claim 1, further comprising anti-cancer active ingredients.

10. The pharmaceutical composition according to claim 9, wherein the anti-cancer active ingredients are selected from the group consisting of cis-platinum, 5-FU, vincristine, taxol and antitumor antibiotics.

11. The pharmaceutical composition according to claim 1, wherein the ratio by weight of the stabilizer to the active ingredient is 1:0.1 to 5, or 1:0.2 to 2.

12. The pharmaceutical composition according to claim 1, wherein said pharmaceutical composition is in a form selected from the group consisting of a tablet, pill, capsule, powder, granule, emulsion, suspension, solution, syrup, elixir, injection, suppository and patch.

13. The pharmaceutical composition according to claim 1, wherein said pharmaceutical composition is in an orally administered solid form, and wherein
the pharmaceutically acceptable salt of N-{4-[3-chloro-4-(3-fluoro-benzyloxy) phenylamino]quinazolin-6-yl}-acrylamide is present in an amount of from 0.1% to 50% by weight, based on the total weight of the composition,
the carrier is one or more selected from the group consisting of a filler, a disintegrant, a wetting agent, a binder, a lubricant, a flavoring agent, an odor-masking agent, and a colorant, and
the weight ratio of the stabilizer to the active ingredient is 1:0.5 to 10, 1:0.5 to 5 or 1:0.5 to 2.

14. The pharmaceutical composition according to claim 13, wherein:
the filler is one or more selected from the group consisting of starch, dextrin, sucrose, lactose, fructose, glucose, xylitol, mannitol, calcium carbonate, magnesium carbonate, calcium phosphate, calcium hydrogen phosphate, calcium sulphate, magnesium oxide and aluminum hydroxide;
the disintegrant is one or more selected from the group consisting of starch, sodium carboxymethyl starch, hydroxypropyl starch, cross-linked sodium carboxymethylcellulose, cross-linked polyvinylpyrrolidone, hydroxypropylmethyl cellulose and an effervescent disintegrant;
the wetting agent is selected from the group consisting of distilled water, ethanol, or combination thereof;
the binder is one or more selected from the group consisting of hydroxypropyl methylcellulose, polyvinylpyrrolidone, starch slurry, dextrin, glucose and molasses thereof, sucrose and molasses thereof, lactose and molasses thereof, fructose and molasses thereof, sorbitol, gelatin mucilage, arabic mucilage, tragacanth mucilage, microcrystalline cellulose, methyl cellulose, sodium carboxymethylcellulose, ethyl cellulose, hydroxypropyl cellulose, and hydroxyethyl cellulose; and
the lubricant is one or more selected from the group consisting of stearic acid, calcium stearate, magnesium stearate, zinc stearate, talc, glyceryl monostearate, glyceryl palmitostearate, magnesium dodecyl sulfate, PEG4000, PEG6000, and sodium stearylfumarate.

15. The pharmaceutical composition according to claim 13, wherein said pharmaceutical composition is in the form of a tablet, and wherein the stabilizer is amylum pregelatinisatum, and the rest of the carrier materials include amylum pregelatinisatum and microcrystalline cellulose as the filler; crosslinked polyvinylpyrrolidone as the disintegrant; and stearic acid and/or talc as the lubricant.

16. The pharmaceutical composition according to claim 13, comprising, by weight, from 10% to 30% of the pharmaceutically acceptable salt of N-{4-[3-chloro-4-(3-fluoro-benzyloxy)phenylamino]quinazolin-6-yl}-acrylamide, from 5% to 60% of the amylum pregelatinisatum as the stabilizer, and wherein the rest of the carriers in the pharmaceutical composition are, by weight, from 10% to 50% of the filler amylum pregelatinisatum, from 5% to 60% of microcrystalline cellulose, from 2% to 15% of crosslinked polyvinylpyrrolidone, from 0% to 10% of stearic acid, and from 0% to 5% of talc, based on the weight of the pharmaceutical composition.

17. The pharmaceutical composition according to claim 13, wherein said pharmaceutical composition is in the form of a tablet, and wherein the stabilizer is poloxamer 188 and the other carriers include microcrystalline cellulose as the filler; crosslinked sodium carboxymethylcellulose as the disintegrant; and magnesium stearate as the lubricant.

18. The pharmaceutical composition according to claim 13 comprising, by weight, from 5% to 15% of the pharmaceutically acceptable salt of N-{4-[3-chloro-4-(3-fluoro-benzyloxy)phenylamino]quinazolin-6-yl}-acrylamide, from 2.5% to 50% of poloxamer 188, from 2% to 60% of microcrystalline cellulose, from 5% to 25% of crosslinked sodium carboxymethylcellulose, and from 3% to 10% of magnesium stearate, based on the weight of the pharmaceutical composition.

19. The pharmaceutical composition according to claim 13, wherein pharmaceutical said composition is in the form of a liquid, and wherein the pharmaceutically acceptable salt of N-{4-[3-chloro-4-(3-fluoro-benzyloxy) phenylamino] quinazolin-6-yl}-acrylamide is present in an amount of from 0.1% to 50% by weight, based on the total weight of the pharmaceutical composition, wherein the carrier includes one or more substances selected from the group consisting of a solvent, a pH regulator, an isotonic regulator, a flavoring agent, an odor-masking agent, a colorant, a preservative and an antioxidant, and wherein the weight ratio of the stabilizer to the active ingredient is 1:0.1 to 5, or 1:0.1 to 2 or 1:0.2 to 2.

20. The pharmaceutical composition according to claim 19, wherein the solvent is one or more selected from the group consisting of water, glycerol, propanediol, polyethylene glycols, $C_1$ to $C_6$ fatty alcohols and fatty oils.

21. The pharmaceutical composition according to claim 19, wherein said pharmaceutical composition is in an oral administered liquid form.

22. The pharmaceutical composition according to claim 19, wherein said pharmaceutical composition is in an oral administered liquid form, and wherein the pharmaceutically acceptable salt N-{4-[3-chloro-4-(3-fluoro-benzyloxy)phenylamino]quinazolin-6-yl}-acrylamide as the active ingredient is present in an amount of from 0.1% to 50% or 0.5% to 30%, or 0.5% to 20% by weight based on the weight of the composition and the weight ratio of the stabilizer to the active ingredient is 1:0.1 to 5 or 1:0.2 to 2.

23. The pharmaceutical composition according to claim 22, wherein, based on the weight of the composition, the pharmaceutically acceptable salt of N-{4-[3-chloro-4-(3-fluoro-benzyloxy)phenylamino]quinazolin-6-yl}-acrylamide is present in an amount of from 0.5% to 20% by weight, the stabilizer is present in an amount of from 2.5% to 30% by weight, the preservative is present in an amount of from 0.1% to 10% by weight, the antioxidant is present in an amount of from 0.1% to 10% by weight, and the solvent is present in an amount of from 30% to 90% by weight.

24. The pharmaceutical composition according to claim 22, wherein the stabilizer is poloxamer 188, and the other carriers include sodium sulfite as the antioxidant, ethyl parahydroxybenzoate as the preservative, and glycerol and distilled water as the solvent.

25. A pharmaceutical composition comprising a pharmaceutically acceptable salt N-{4-[3-chloro-4-(3-fluoro-benzyloxy)phenylamino]quinazolin-6-yl}-acrylamide as an active ingredient and optionally a pharmaceutically applicable carrier or diluent, and a stabilizer having a dispersing and/or protective effect on the active ingredient, wherein the ratio by weight of the stabilizer to the active ingredient is 1:0.1 to 10, and wherein the active ingredient is crystalline form A, crystalline form B, or crystalline form C of N-{4-[3-chloro-4-(3-fluoro-benzyloxy)phenylamino]quinazolin-6-yl}-acrylamide p-toluene sulfonate, or mixtures thereof.

26. The pharmaceutical composition according to claim 25, wherein the stabilizer having a dispersing and/or protective effect on the active ingredient is one or more selected from the group consisting of hydroxypropyl methyl cellulose, hydroxypropyl cellulose, calcium carboxymethyl cellulose, sodium carboxymethyl cellulose, methyl cellulose, hydroxyethyl cellulose, povidone, sodium dodecyl sulphonate, amylum pregelatinisatum, microcrystalline cellulose, polyethylene glycols, dioctyl sulfosuccinate, gelatin, arabic gum, tragacanth, stearic acid, calcium stearate, lecithin, dextran, cholesterol, glycerol monostearate, sorbitan esters, polyoxyethylene alkyl ethers, polyoxyethylene castor oil derivatives, polyoxyethylene sorbitan fatty acid esters, polyoxyethylene stearate, polyvinyl alcohol, poloxamers, colloidal silicon dioxide, magnesium aluminum silicate, alginate, chitosan and polylysine.

27. The pharmaceutical composition according to claim 26, with the proviso that when the composition is prepared, the stabilizer and the active ingredient are firstly homogenously mixed and subsequently mixed with the pharmaceutically applicable carrier or diluent.

\* \* \* \* \*